United States Patent
Ogawa (10) Patent No.: US 6,682,486 B2
(45) Date of Patent: Jan. 27, 2004

(54) ULTRASONIC DIAGNOSING METHOD AND APPARATUS USING CORRELATIVE COEFFICIENT

(75) Inventor: Eiji Ogawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/098,382

(22) Filed: Mar. 18, 2002

(65) Prior Publication Data

US 2002/0138005 A1 Sep. 26, 2002

(30) Foreign Application Priority Data

Mar. 21, 2001 (JP) ........................ 2001-079776

(51) Int. Cl.[7] ............................................... A61B 8/00
(52) U.S. Cl. ........................................................ 600/443
(58) Field of Search ................................. 600/407–471; 367/7, 11, 130, 138; 73/625, 626; 128/916; 369/59.26, 48, 49, 50

(56) References Cited

U.S. PATENT DOCUMENTS 5,717,670 A * 2/1998 Mitsuno ................... 369/59.26

FOREIGN PATENT DOCUMENTS

JP 2676014 7/1997

* cited by examiner

Primary Examiner—Ali M. Imam
(74) Attorney, Agent, or Firm—Sughrue Mion, PLLC (57) ABSTRACT

An ultrasonic diagnosing apparatus capable of obtaining ultrasonic images in high precision even in such a case where waveforms of ultrasonic waves are deformed in transmission and reception stages. The ultrasonic diagnosing apparatus includes: an ultrasonic wave transmitting unit; an ultrasonic wave receiving unit; a signal processing unit for processing the detection signals to thereby produce data; a first storage unit for storing data obtained by transmitting/receiving ultrasonic waves to/from a first object; a second storage unit for storing data obtained by transmitting/receiving ultrasonic waves to/from a second object; a correlative coefficient calculating unit for calculating a correlative coefficient between the data stored in the first storage unit and in the second storage unit; an image processing unit for producing an image signal based upon the correlative coefficient; and an image display unit for displaying an ultrasonic diagnostic image based upon the image signal.

15 Claims, 7 Drawing Sheets

ULTRASONIC DIAGNOSING METHOD AND APPARATUS USING CORRELATIVE COEFFICIENT

BACKGROUND OF THE INVENTION

1. Field of the Invention

The present invention generally relates to an ultrasonic diagnosing method and an ultrasonic diagnosing apparatus, capable of transmitting ultrasonic waves to an object to be inspected and receiving ultrasonic echoes reflected from the object so as to display an ultrasonic diagnostic image of the object on the basis of the reflected ultrasonic echoes. More specifically, the present invention is directed to such ultrasonic diagnosing method and apparatus capable of displaying ultrasonic diagnostic images having a better S/N ratio by calculating a correlative coefficient between data which are obtained by detecting ultrasonic echoes reflected from first and second objects.

2. Description of a Related Art

Figure 7A:
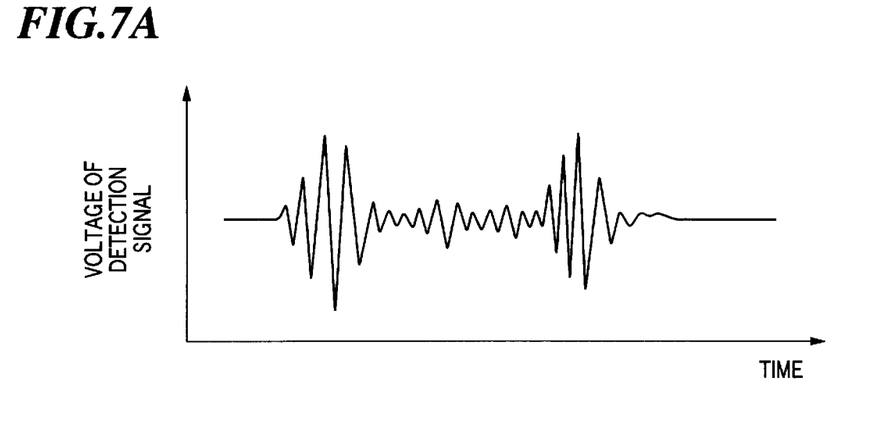
FIGS. 7A to 7C are waveform diagrams showing a detection signal and so on which are processed in the conventional ultrasonic diagnosing apparatus.
Figure 7B:
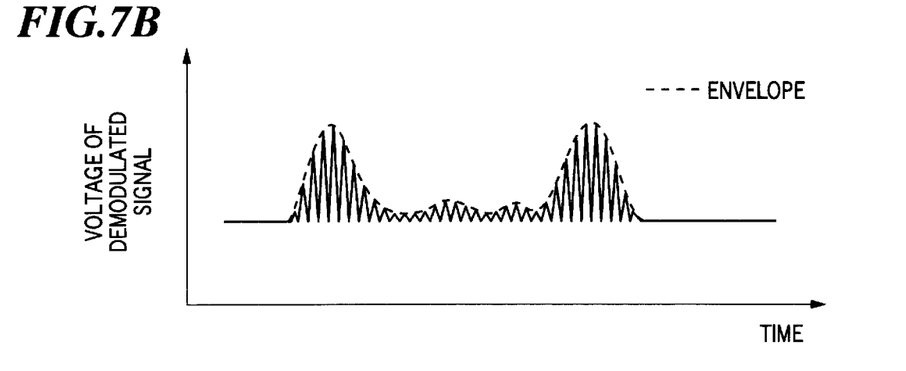
Figure 7C:
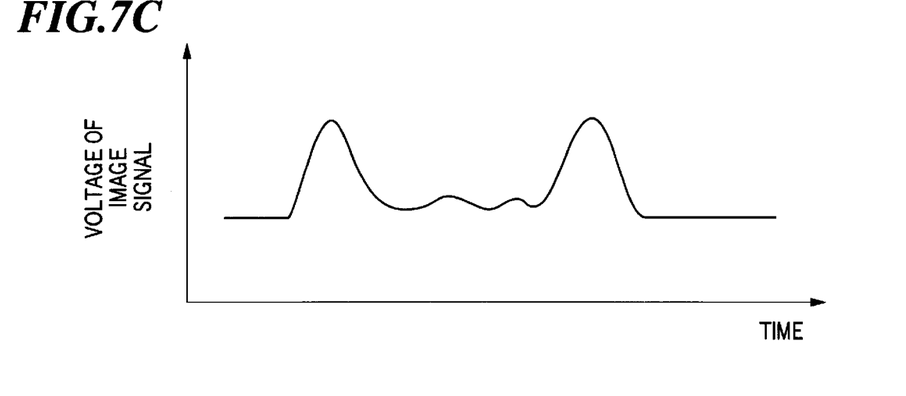

In conventional ultrasonic diagnosing apparatus, ultrasonic transducer elements such as PZT (Pb(lead) zirconate titanate) are employed in order to receive ultrasonic echoes. FIGS. 7A to 7C show waveforms of detection signals which are processed in one conventional ultrasonic diagnosing apparatus. An ultrasonic transducer element which receives ultrasonic waves (ultrasonic echoes) outputs such a detection signal as shown in FIG. 7A. This ultrasonic detection signal is demodulated to obtain such a demodulated signal as shown in FIG. 7B.

Furthermore, since this demodulated signal is filtered by employing a low-pass filter, an envelope signal as shown in FIG. 7C is extracted from the demodulated signal. In this case, an "envelope" implies such a line formed by connecting maximal values of the demodulated signal.

Generally speaking, such an envelope signal is employed as an image signal. However, all components of the detection signal or the demodulated signal are equivalently utilized, so that the image signal obtained in the above-described signal process manner may be easily and adversely influenced by noise.

On the other hand, Japanese patent No. 2676014 (will be also referred to as Document 1 hereinafter) describes the below-mentioned technique. According to the technique, ultrasonic pulse signals transmitted from respective ultrasonic transmitting elements are phase-modulated by using a modulating signal which is constituted in accordance with such an orthogonal function as Walsh function, and correlative coefficients between respective reception waves and a transmission signal are obtained. As a result, it is no longer necessary to scan the interior of the target space. That is, the ultrasonic pulse signals can be transmitted to the interior of this target space at the same time, and therefore, a time duration required to obtain a single ultrasonic image can be considerably shortened.

In accordance with the technique described in Document 1, the time duration required to obtain a single ultrasonic image can be shortened because the interior of the target space is not scanned. However, in such a case where the waveforms of the ultrasonic waves are deformed due to attenuation and scattering phenomena occurred in the ultrasonic wave transmission/reception stages, the correlative coefficients between the respective reception waves and the transmission signal are decreased.

Also, Document 1 discloses the ultrasonic wave transmitting method used in an ultrasonic imaging apparatus. In the ultrasonic wave transmitting method, while pulse-shaped ultrasonic waves are transmitted toward a target space at the same time from a plurality of non-directional ultrasonic-wave transmitting elements arranged in a two-dimensional manner, the scattered waves which are produced by scattering the pulse-shaped ultrasonic waves within the interior of the target space are received by a plurality of non-directional ultrasonic-wave receiving elements. Based upon the signal strengths and also the elapse time from the transmitting operation of this ultrasonic pulse signal to the receiving operation thereof, distribution of the scattering points of ultrasonic waves within the target space is calculated. In accordance with this ultrasonic wave transmitting method, ultrasonic transmission signals are phase-modulated by using modulating signals which are constituted in accordance with orthogonal functions. This phase modulation is carried out by employing the modulating signals which are different from each other for every ultrasonic wave transmitting element. Moreover, while combinations between the phase modulating signals and the ultrasonic wave transmitting elements are changed for every ultrasonic transmitting element, the ultrasonic waves are transmitted plural times in such a time interval during which these ultrasonic waves never interfere with each other. Both the numbers of the ultrasonic wave transmitting elements and the sequential orders of the ultrasonic wave transmissions are converted into binary number indications to obtain exclusive-OR result thereof for every bit. Then, such an ultrasonic wave having an orthogonal function number corresponding to the exclusive-OR result is transmitted from the ultrasonic wave transmitting elements. The distribution of the scattering points can be calculated by receiving the ultrasonic waves plural times.

According to the ultrasonic wave transmitting method used in the ultrasonic imaging apparatus disclosed in the above-described Document 1, while occurrence of an artifact image can be prevented, an ultrasonic image can be obtained in high precision. However, in such a case where the waveforms of the ultrasonic waves are deformed due to s and scattering phenomena occurred in the ultrasonic wave transmission/reception stages, the correlative coefficients between the respective ultrasonic reception waves and the ultrasonic transmission signals are decreased.

SUMMARY OF THE INVENTION

The present invention has been made to solve such a problem of the conventional technique. An object of the present invention is therefore to provide ultrasonic diagnosing method and apparatus capable of obtaining an ultrasonic image in high precision even when waveforms of ultrasonic waves are deformed due to attenuation and scattering phenomena occurred in ultrasonic wave transmission/reception stages.

To solve the above-described problem of the prior art, an ultrasonic diagnosing apparatus according to one aspect of the present invention comprises: ultrasonic wave transmitting means for transmitting ultrasonic waves each having a predetermined waveform; ultrasonic wave receiving means for receiving ultrasonic echoes reflected from an object to be inspected to thereby output detection signals; signal processing means for processing the detection signals derived from the ultrasonic wave receiving means to thereby produce data; first storage means for storing data which is obtained by transmitting ultrasonic waves to a first object and receiving ultrasonic echoes reflected from the first object; second storage means for storing data which is obtained by transmitting ultrasonic waves to a second object and receiving ultrasonic echoes reflected from the second object; correlative coefficient calculating means for calculating a correlative coefficient between the data stored in the first storage means and the data stored in the second storage means; image processing means for producing an image signal based upon the correlative coefficient calculated by the correlative coefficient calculating means; and an image display unit for displaying an ultrasonic diagnostic image based upon the image signal produced by the image processing means.

Also, an ultrasonic diagnosing method according to one aspect of the present invention comprises the steps of: (a) storing data which is obtained by transmitting ultrasonic waves each having a predetermined waveform to a first object and receiving ultrasonic echoes reflected from the first object; (b) storing data which is obtained by transmitting ultrasonic waves each having a predetermined waveform to a second object and receiving ultrasonic echoes reflected from the second object; (c) calculating a correlative coefficient between the data stored at step (a) and the data stored at step (b); (d) producing an image signal based upon the correlative coefficient calculated at step (c); and (e) displaying an ultrasonic diagnostic image based upon the image signal produced at step (d).

As a consequence, according to the ultrasonic diagnosing method/apparatus of the present invention, the correlative coefficient between the data obtained by detecting ultrasonic echoes reflected from the first object and the data obtained by detecting ultrasonic echoes reflected from the second object is calculated, so that the ultrasonic image signals may not be easily nor adversely influenced by the noise. As a consequence, even in the case where the ultrasonic waves are attenuated or scattered, the large correlative coefficients can be obtained, so that the ultrasonic images having the superior S/N ratios can be obtained.

BRIEF DESCRIPTION OF THE DRAWINGS

A more better understanding of the present invention may be made by reading a detailed description to be read in conjunction with the accompanying drawings, in which.

DESCRIPTION OF THE PREFERRED EMBODIMENTS

Referring now to drawings, various preferred embodiments of the present invention will be described in detail. It should be understood that the same reference numerals will be employed as those for indicating the same, or similar structural elements, and therefore, descriptions thereof are omitted.

Figure 1:
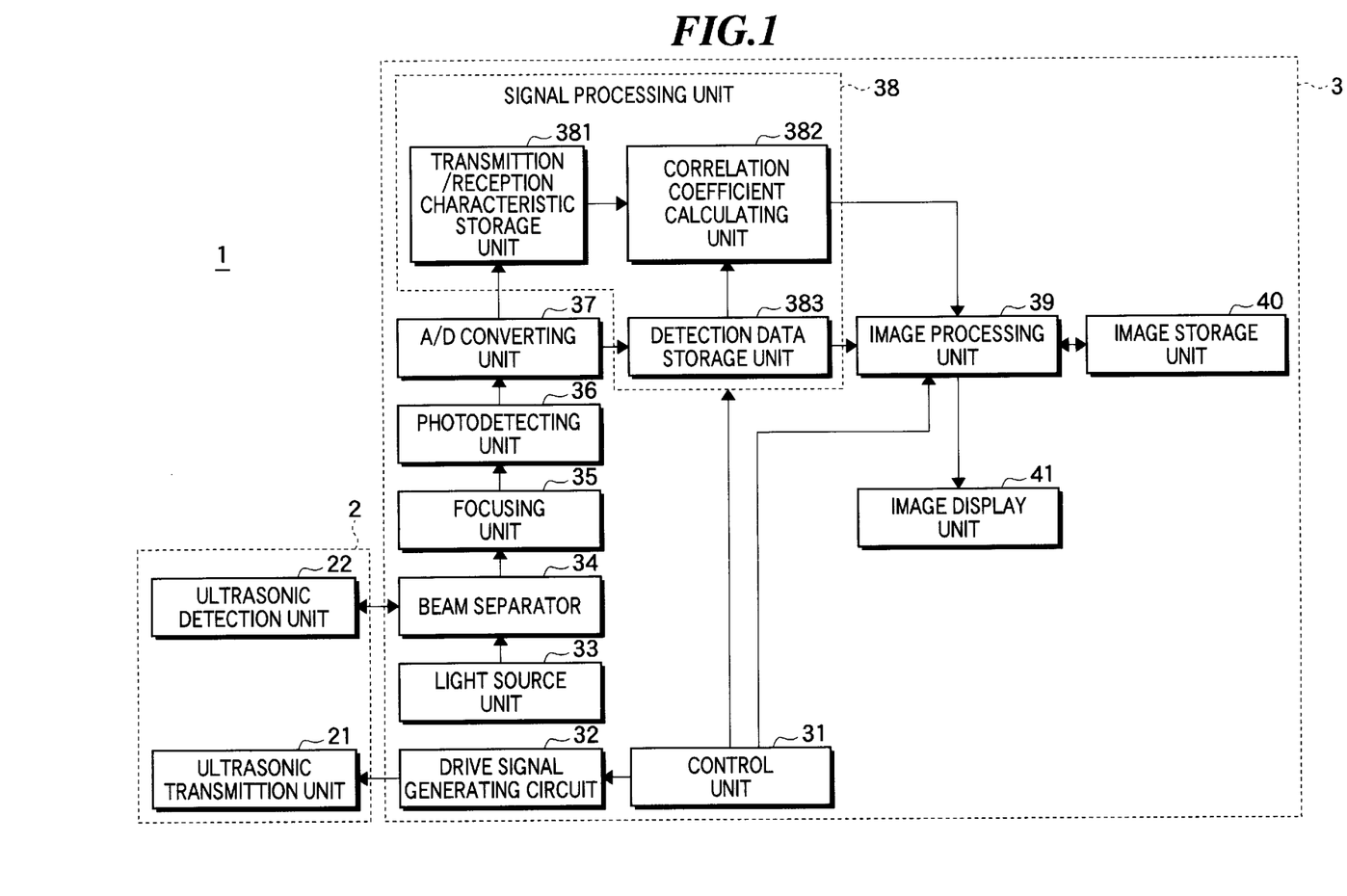
FIG. 1 is a block diagram schematically showing an arrangement of an ultrasonic diagnosing apparatus according to one embodiment of the present invention.

FIG. 1 is a schematic diagram showing an arrangement of an ultrasonic diagnosing apparatus according to one embodiment of the present invention. The ultrasonic diagnosing apparatus 1 may be provided with an ultrasonic probe 2 and a main body 3, as shown in FIG. 1.

The ultrasonic probe 2 includes an ultrasonic wave transmitting unit 21 and an ultrasonic wave detecting unit 22. The ultrasonic wave transmitting unit 21 owns transducers capable of transmitting ultrasonic waves in accordance with drive signals supplied from the main body 3. The ultrasonic wave detecting unit 22 owns optical modulating elements (ultrasonic wave detecting elements) capable of modulating light entered from the main body 2 in accordance with applied ultrasonic waves. In this ultrasonic wave transmitting unit 21, as the ultrasonic transducer, for example, piezoelectric elements are employed which involve piezoelectric ceramics typically known as PZT (Pb(lead) zirconate titanate) and a polymer piezoelectric element typically known as PVDF (polyvinyl difluoride). Also, the ultrasonic wave detecting unit 22 may include such an optical modulating element as an optical fiber array for transferring therethrough light entered from the main body 2 and, either an FPR (Fabry-Perot resonator) or an FBG (fiber Bragg grating), which is mounted on a tip portion of each of optical fibers.

The main body 3 includes a control unit 31, a drive signal generating circuit 32, a light source unit 33, a beam separator 34, a focusing unit 35, a photo-detecting unit 36, an A/D (analog-to-digital) converting unit 37, a signal processing unit 38, an image processing unit 39, an image storage unit 40, and an image displaying unit 41. Also, the signal processing unit 38 includes a transmission/reception characteristic storage unit 381, a correlative coefficient calculating unit 382, and a detection data storage unit 383.

The control unit 31 controls operation timing of the drive signal generating circuit 32 and operation timing of the signal processing unit 38, and also controls the respective structural units of this main body 3.

The drive signal generating circuit 32 outputs a drive signal used to drive the ultrasonic wave transmitting unit 21 under control of the control unit 31. The drive signal output from the drive signal generating circuit 32 is used to drive the ultrasonic wave transmitting unit 21 to output ultrasonic waves having predetermined pulse waveforms.

The light source unit 33 produces light having a predetermined wavelength.

The beam separator 34 causes the light projected from the light source unit 33 to be penetrated through the own beam separator 34 toward a direction of the ultrasonic wave detecting unit 22, and also reflects a portion of light entered from a direction of the ultrasonic wave detecting unit 22 so as to conduct this reflected light toward a direction of the focusing unit 35.

The photo-detecting unit 36 includes a plurality of PDs (photodiodes) or a CCD (charge-coupled device), which may convert received light into an electric signal.

The focusing unit 35 focuses the light entered from the beam separator 34 onto a light receiving plane of the photo-detecting unit 36.

The A/D converting unit 37 converts an analog signal (detection signal) output from the photo-detecting unit 36 into a digital signal (detection data or demodulated data).

The transmission/reception characteristic storage unit 381 stores thereinto the data received from the A/D converting unit 37 when a transmission/reception characteristic storage operation is carried out before the normal imaging operation is performed.

The detection data storage unit 383 stores thereinto the data received from the A/D converting unit 37 while the normal imaging operation is carried out.

The correlative coefficient calculating unit 382 calculates such a correlative coefficient $R(\tau)$ between the data which is stored in the transmission/reception characteristic storage unit 381 and the data which is stored in the detection data storage unit 383.

It should also be noted that the correlative coefficient $R(\tau)$ may be calculated by employing a self-correlative function $C(\tau)$ on the basis of the below-mentioned equation:

$$R(\tau)=C(\tau)/C(0)$$

where symbol "$\tau$" indicates delay time. In connection with this equation, the above-described self-correlative function $C(\tau)$ is expressed by:

$$C(\tau) = \int_{-\infty}^{\infty} x(t)x(t-\tau)\,dt$$

In the ultrasonic diagnosing apparatus of this embodiment, the correlative coefficient calculating unit 382 may calculate the correlative coefficient $R(\tau)$ in such a manner that while the data stored in the transmission/reception characteristic storage unit 381 and the data stored in the detection data storage unit 383 are slightly shifted (namely, this data shift corresponds to changing of delay time "$\tau$"), these shifted data are multiplied with each other and then the multiplied data are added cumulatively.

The image processing unit 39 produces an image signal (image data) by multiplying the correlative coefficient calculated by the correlative coefficient calculating unit 382 by the data stored in the detection data storage unit 383.

The image storage unit 40 stores thereinto the image signal produced by the image processing unit 39.

The image display unit 41 displays thereon an ultrasonic image in response to the image signal produced by the image processing unit 39.

Next, various operations of the above-described ultrasonic diagnosing apparatus according to one embodiment of the present invention. This ultrasonic diagnosing apparatus 1 may perform both an ultrasonic transmission/reception characteristic storage operation and the normal ultrasonic imaging operation. In the ultrasonic transmission/reception characteristic storage operation, ultrasonic transmission/reception characteristics of the diagnostic apparatus 1 are measured and stored. In the normal ultrasonic imaging operation, an image of an object to be inspected is ultrasonically imaged for the normal ultrasonic diagnosis. These operations are carried out under control of the control unit 31 in accordance with instructions issued by an operator.

Figure 2:
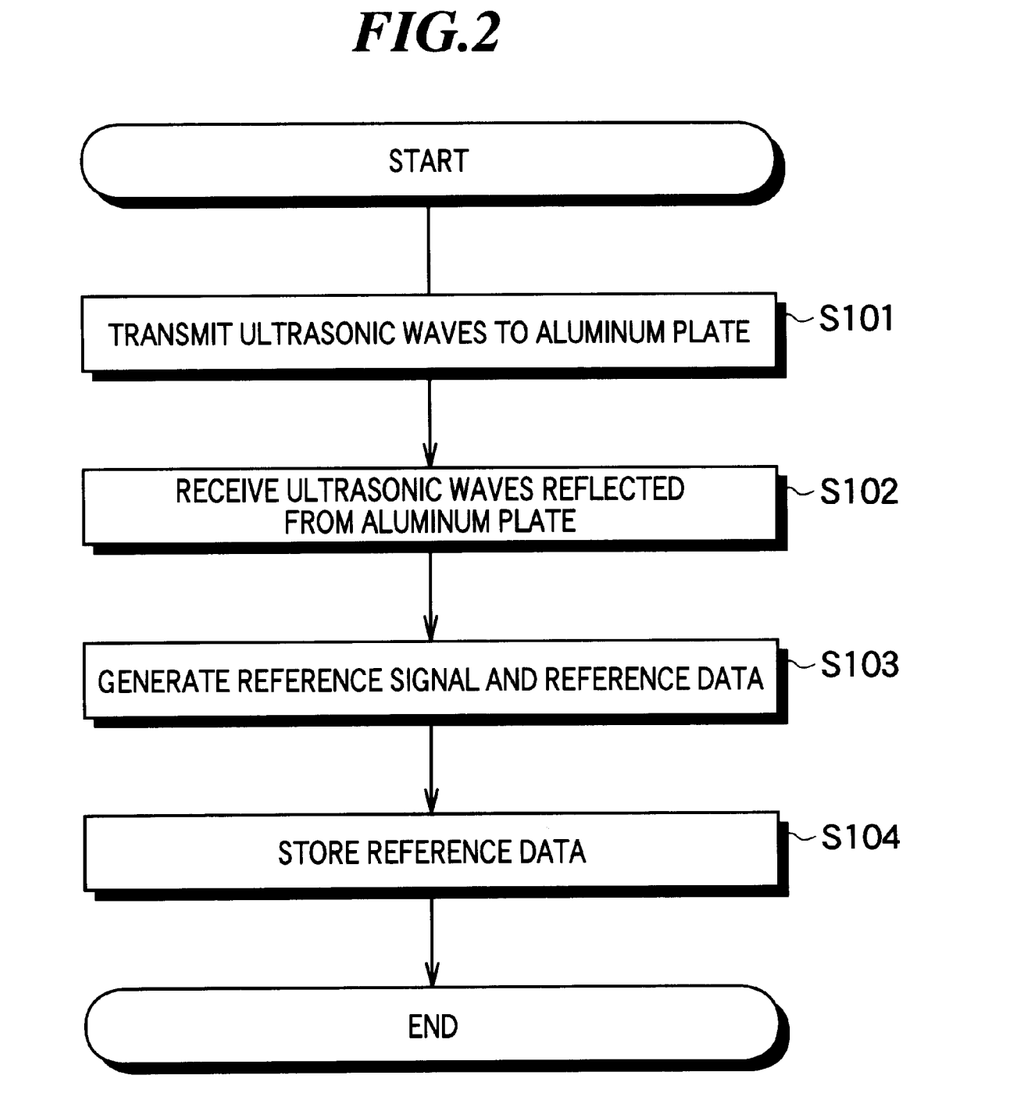
FIG. 2 is a flow chart showing storage operations of transmission/reception characteristic as to the ultrasonic diagnosing apparatus according to one embodiment of the present inventions.

First, a description will now be made of the ultrasonic transmission/reception characteristic storage operation of the ultrasonic diagnosing apparatus 1 with reference to FIGS. 1 and 2. FIG. 2 is a flow chart showing the ultrasonic transmission/reception characteristic storage operation executed by this ultrasonic diagnosing apparatus 1. In this transmission/reception characteristic storage operation, such an ultrasonic reflection article is employed by which a predetermined reception effect (result) can be obtained with respect to a transmission of a predetermined ultrasonic wave to this ultrasonic reflection article. In this embodiment, an aluminum plate is employed as such an ultrasonic reflection article.

For instance, when an operator holds the ultrasonic probe 2 of the ultrasonic diagnosing apparatus 1 in such a manner that this ultrasonic probe 2 is located opposite to such an aluminum plate installed within a fluid such as water and instructs the ultrasonic diagnosing apparatus 1 to commence the transmission/reception characteristic storage operation, this ultrasonic diagnosing apparatus 1 commences a series of ultrasonic transmission/reception characteristic storage operation as explained in the flow chart of FIG. 2.

Figure 4A:
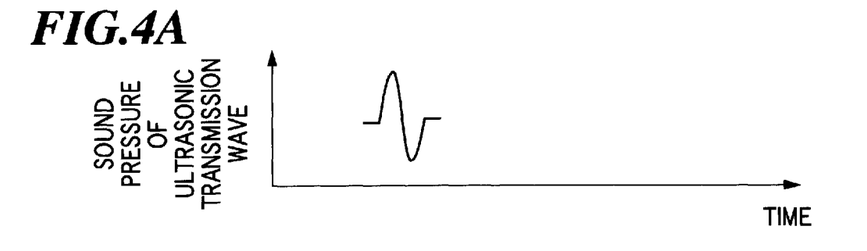
FIGS. 4A to 4E are waveform diagrams showing a waveform and so on of ultrasonic waves which are transmitted and received by the ultrasonic diagnosing apparatus according to one embodiment of the present invention.

In the ultrasonic transmission/reception storage operation, the drive signal generating circuit 32 generates a drive signal and supplies this drive signal to the ultrasonic wave transmitting unit 21 under control of the control unit 31. The ultrasonic wave transmitting unit 21 transmits an ultrasonic wave having a predetermined waveform to the aluminum plate in accordance with the drive signal (step S101). In this embodiment, an ultrasonic wave having such a pulse waveform as shown in FIG. 4A is transmitted. The ultrasonic wave transmitted from the ultrasonic wave transmitting unit 21 is propagated through the water to be reflected on the aluminum plate, and then, the reflected ultrasonic echo is received by the ultrasonic detecting unit 22 (step S102).

In the ultrasonic wave detecting unit 22, the light having the predetermined wavelength, which is produced by the light source unit 33, is modulated by the received ultrasonic echo. The direction of this modulated light is changed by the beam separator 34, and the resultant light passes through the focusing unit 35, and thereafter, this light is focused onto the detection plane of the photo-detecting unit 36.

At step S103, the photo-detecting unit 36 produces an analog electric signal (detection signal) on the basis of the light focused onto the detection plane thereof, and then, the A/D converting unit 37 converts this analog detection signal into a digital signal (data). In this embodiment, such a detection signal which is obtained in the ultrasonic transmission/reception characteristic storage operation will be referred to as a "reference signal", whereas data which is converted from this reference signal will be referred to as "reference data".

At step S104, the transmission/reception characteristic storage unit 381 stores thereinto the reference data.

Figure 4B:
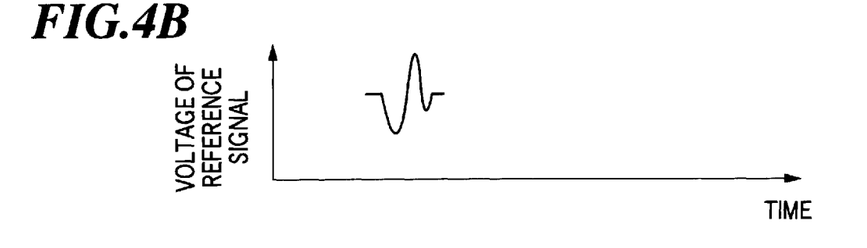

FIG. 4B represents an example of a waveform of this reference signal. The reference signal may be preferably obtained in correspondence with a position of each of sound rays. The reference signal obtained in such a manner may be conceived to contain components representative of ultrasonic transmission/reception characteristics of ultrasonic wave transmitting/receiving system circuits. The ultrasonic wave transmitting/receiving system circuits include both ultrasonic wave transmitting system circuits (namely, drive signal generating circuit 32 and ultrasonic wave transmitting unit 21) and ultrasonic wave receiving system circuits (namely, ultrasonic detecting unit 22, beam separator 34, focusing unit 35 and photo-detecting unit 36) employed in the ultrasonic diagnosing apparatus 1.

Figure 3:
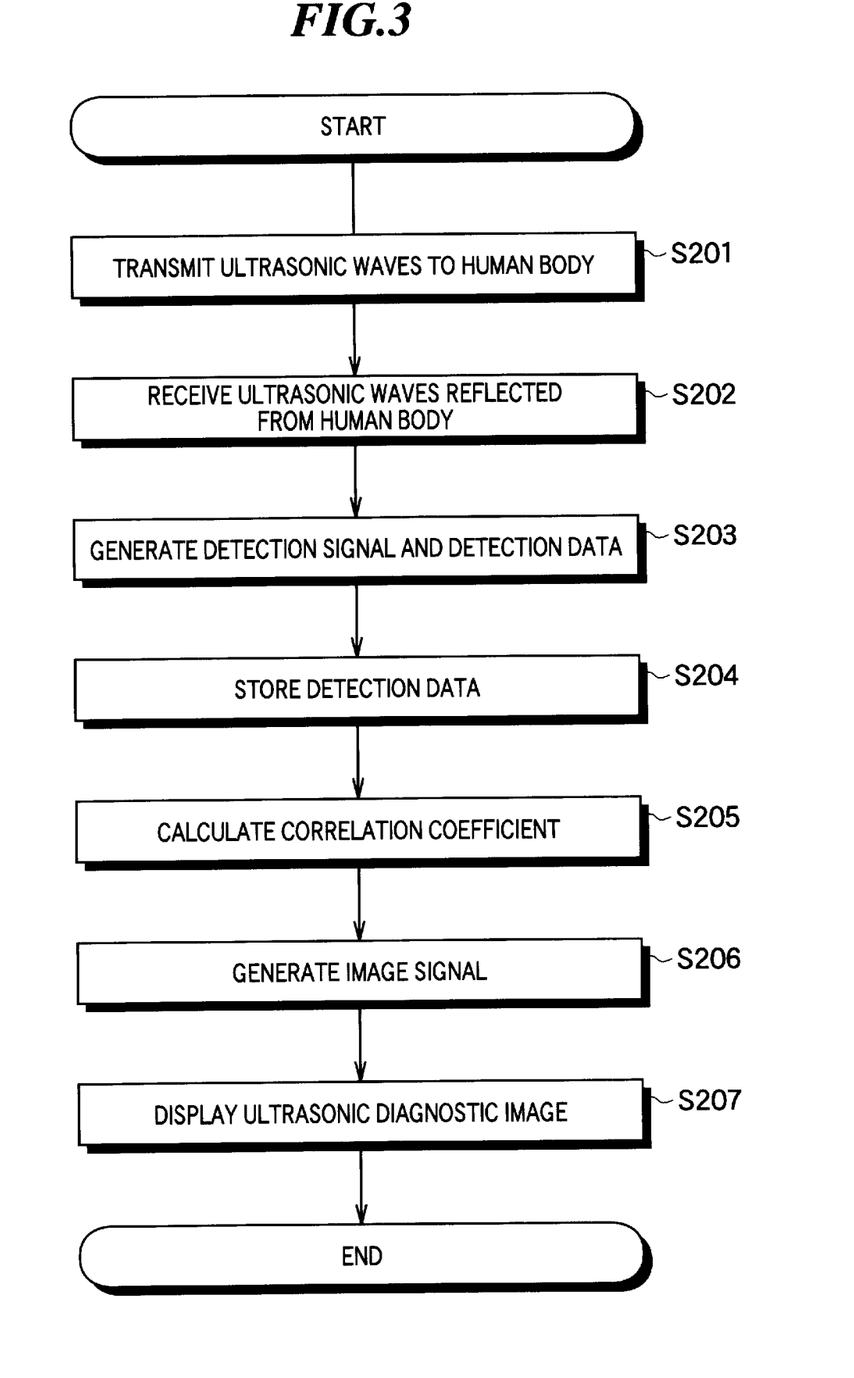
FIG. 3 is a flow chart showing the normal imaging operation of the ultrasonic diagnosing apparatus according to one embodiment of the present invention.

Referring now to FIGS. 1 and 3, normal imaging operation of the ultrasonic diagnosing apparatus 1 according to this embodiment will be explained. FIG. 3 is a flow chart showing this normal imaging operation of the ultrasonic diagnosing apparatus 1.

When the operator depresses the ultrasonic probe 2 of the ultrasonic diagnosing apparatus 1 against a human body as an object of ultrasonic diagnosis and instructs the ultrasonic diagnosing apparatus 1 to commence the above-described normal imaging operation, this ultrasonic diagnosing apparatus 1 starts a series of such normal imaging operation as described in the flow chart of FIG. 3.

While the normal imaging operation is carried out, the drive signal generating circuit 32 generates a drive signal and supplies this drive signal to the ultrasonic wave transmitting unit 21 under control of the control unit 31, and then, the ultrasonic wave transmitting unit 21 transmits an ultrasonic wave having a preselected waveform to the human body in accordance with this drive signal (step S201). The ultrasonic wave transmitted from the ultrasonic wave transmitting unit 21 is propagated within the human body, and then, is reflected from an organ and the like, and thereafter, the reflected ultrasonic echoes are received by the ultrasonic wave detecting unit 22 (step S202).

In the ultrasonic wave detecting unit 22, the light having the predetermined wavelength, which is generated by the light source unit 33, is modulated by the received ultrasonic echo. The direction of this modulated light is changed by the beam separator 34 and the resultant light passes through the focusing unit 35, and thereafter, this light is focused onto the detection plane of the photo-detecting unit 36.

At step S203, the photo-detecting unit 36 produces an analog electric signal (detection signal) on the basis of the light focused onto the detection plane thereof, and then, the A/D converting unit 37 converts this analog detection signal into a digital signal (data). In this embodiment, such data which is converted from the detection signal obtained during the normal imaging operation will be referred to as "detection data".

Next, the detection data storage unit 383 stores thereinto the detection data (step S204).

Figure 4C:
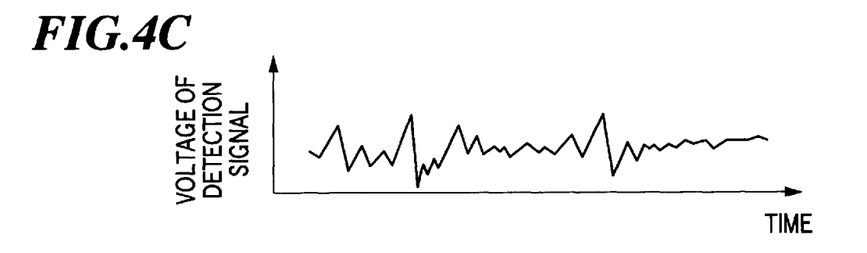

FIG. 4C shows an example of a waveform of the detection signal. The detection signal is produced every sound ray, and the detection data is stored every sound ray.

Figure 4D:
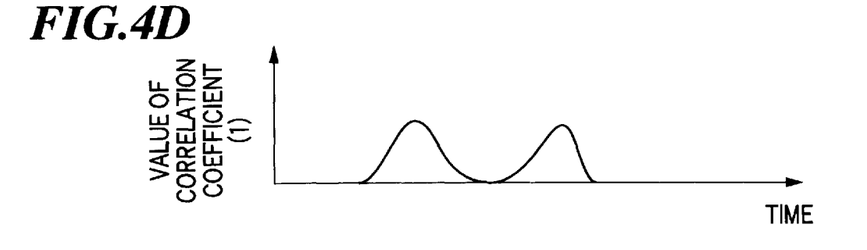
Figure 4E:
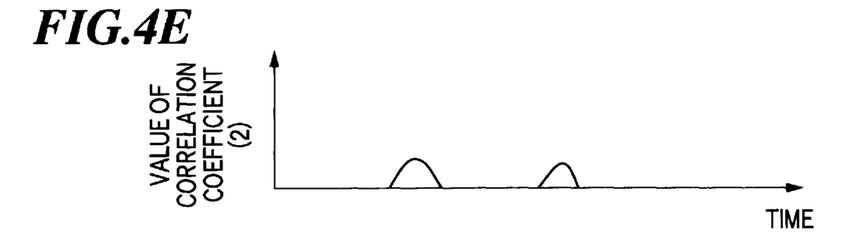

Next, the correlative coefficient calculating unit 382 calculates a correlative coefficient between the reference data stored in the transmission/reception characteristic storage unit 381 and the detection data stored in the detection data storage unit 383 (step S205). FIG. 4D is a diagram showing a correlative coefficient between the reference signal as shown in FIG. 4B and the detection signal as shown in FIG. 4C. Such a correlative coefficient is calculated every sound ray. Further, the correlative coefficient calculating unit 382 may furthermore execute a threshold value processing operation capable of extracting correlative coefficient portions larger than, or equal to a predetermined threshold value with respect to the calculated correlative coefficients. FIG. 4E shows such an example that the threshold value processing operation is performed with respective to the correlative coefficient as shown in FIG. 4D.

Subsequently, the image processing unit 39 multiplies the detection data by the correlative coefficient to produce an image signal (step S206). This image signal is temporarily stored in the image storage unit 40.

Next, the image display unit 41 displays thereon an ultrasonic diagnostic image indicative of the organ and the like contained in the human body based upon the image signal (step S207).

In this embodiment, the detection data is multiplied by the correlative coefficient so as to produce the image signal. Alternatively, the correlative coefficient may be directly employed as such an image signal. Alternatively, the detection data may be multiplied by the correlative coefficient after the threshold value processing operation.

According to this embodiment, the image signal is produced on the basis of the correlative coefficient between the reference data and the detection data, and therefore, the image having the superior S/N ratio can be displayed while considering both the response characteristic of the ultrasonic wave transmission system circuit and also the response characteristic of the ultrasonic wave reception system circuit.

While the ultrasonic diagnosing method and apparatus according to the present invention have been described based upon the above-described embodiments, the present invention is not apparently limited to these embodiments.

For instance, both the ultrasonic wave transmitting unit 21 and the ultrasonic wave detecting unit 22 may be arranged in an integral form by using as the ultrasonic wave detecting element such an element (PZT etc.) capable of transmitting and receiving ultrasonic echoes in the ultrasonic wave detecting unit 22. Even in such an alternative case, an image signal can be produced based upon the reference data and the detection data to display an image having a superior S/N ratio.

Also, in the ultrasonic wave transmitting unit 21, ultrasonic waves may be transmitted and received by employing a phased-array type ultrasonic wave detecting element having a plurality of channels. In this alternative case, either the transmission/reception characteristic storage unit 381 or the detection data storage unit 383 may store as the reference data or the detection data such data which is obtained by matching phases of plural detection signals with each other, which are output from the respective plural channels of ultrasonic wave detecting elements, and the correlative coefficient calculating unit 382 may calculate correlative coefficients between these stored data.

In the embodiment, the signal processing unit 38 is interposed between the A/D converting unit 37 and the image processing unit 39 so as to perform the digital signal processing operation. Alternatively, a signal processing unit may be interposed between the photo-detecting unit 36 and the A/D converting unit 37 to carry out an analog signal processing operation.

Also, in this embodiment, the aluminum plate arranged within the fluid is employed as the article capable of reflecting the ultrasonic wave while the transmission/reception characteristic storage operation is carried out. Instead of this aluminum plate, a phantom or the like may be employed which has acoustic impedance substantially equal to that of a human body.

Figure 5A:
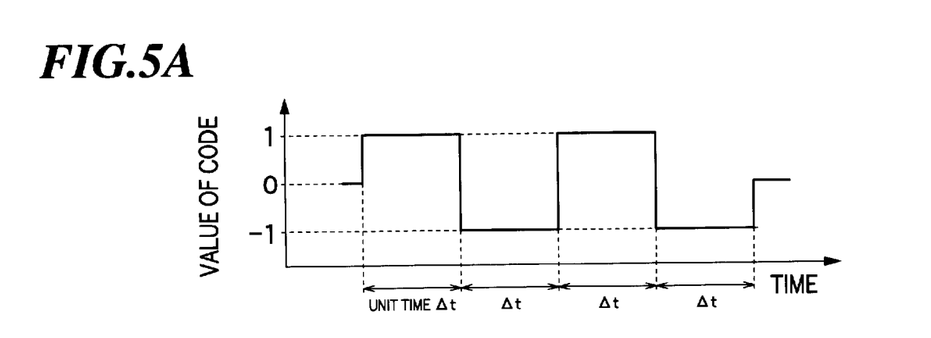
FIGS. 5A to 5C are waveform diagrams showing another waveform and so on of ultrasonic waves which are transmitted and received by the ultrasonic diagnosing apparatus according to one embodiment of the present invention.
Figure 5B:
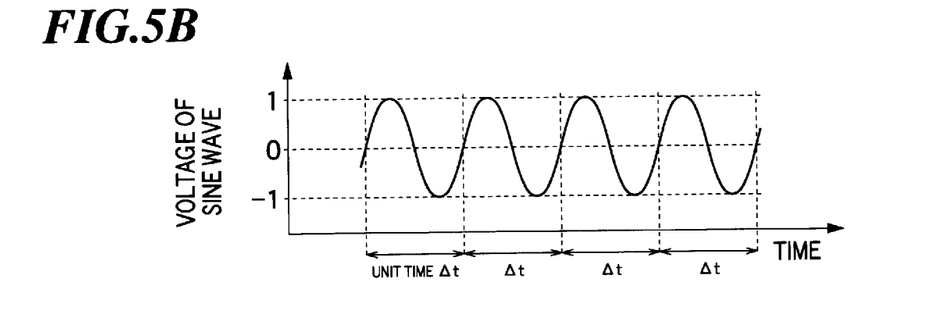
Figure 5C:
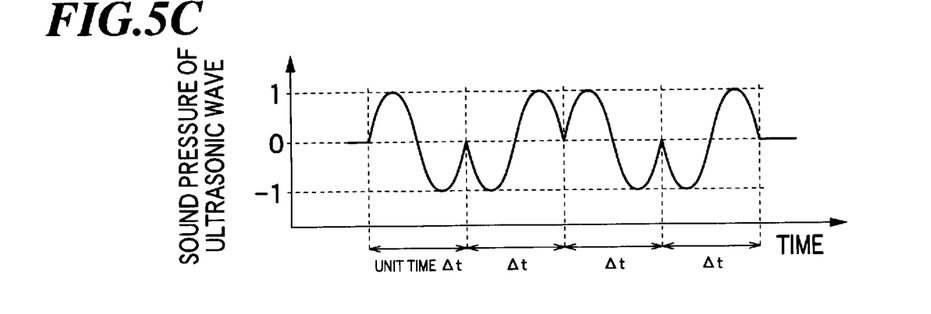
Figure 6A:
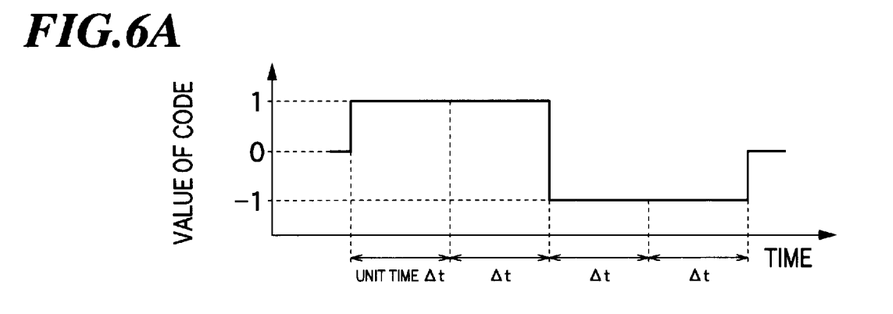
FIGS. 6A to 6C are waveform diagrams showing other waveform and so on of ultrasonic waves which are transmitted and received by the ultrasonic diagnosing apparatus according to one embodiment of the present invention.
Figure 6B:
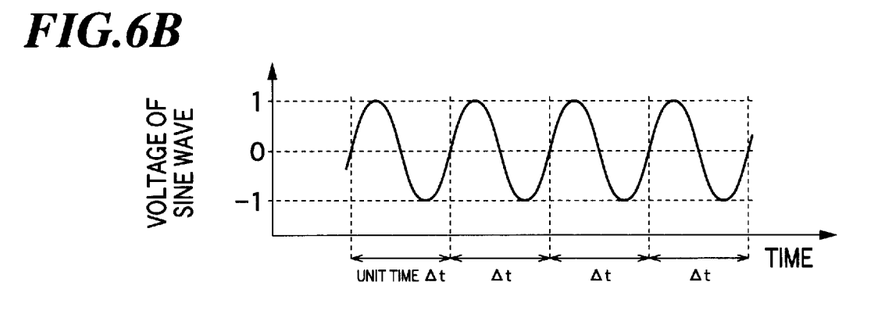
Figure 6C:
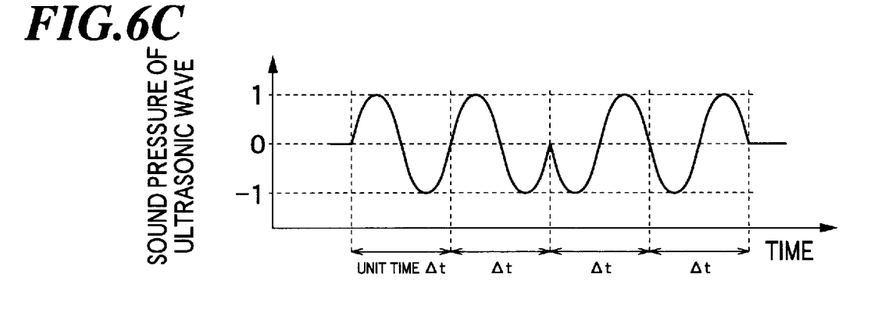

Also, in the embodiment, as shown in FIG. 4A, the ultrasonic wave having the pulse waveform is transmitted from the ultrasonic wave transmitting unit 21. Alternatively, a coded-ultrasonic wave may be transmitted. For instance, when a sine wave as shown in FIG. 5B is modulated based upon a code as shown in FIG. 5A, such a waveform as shown in FIG. 5C may be produced. An ultrasonic wave having such a waveform may be transmitted. Furthermore, for example, when a sine wave as shown in FIG. 6B is modulated by such a code as shown in FIG. 6A, another waveform as shown in FIG. 6C may be produced. Then, an ultrasonic wave having such a waveform may be transmitted. In these alternative cases, when the ultrasonic transmission/reception storage operation is carried out, it is preferable to obtain reference data corresponding to patterns of these codes. In addition, AC (alternating current) waves such as rectangular waves and triangular waves other than the above-explained sine waves may be employed.

As previously described, according to the present invention, since the correlative coefficient between the data obtained by detecting the ultrasonic echo reflected from the first object (for example, aluminum plate) and the data obtained by detecting the ultrasonic echoes reflected from the second object (for example, human body) is calculated, the ultrasonic image signals are hardly influenced by the noise. As a consequence, even in the case where the ultrasonic waves are attenuated and/or scattered, the large correlative coefficients can be obtained, and therefore, the ultrasonic images having the superior S/N ratios can be obtained.

What is claimed is:

1. An ultrasonic diagnosing apparatus comprising:
    ultrasonic wave transmitting means for transmitting ultrasonic waves each having a predetermined waveform;
    ultrasonic wave receiving means for receiving ultrasonic echoes reflected from an object to be inspected to thereby output detection signals;
    signal processing means for processing the detection signals derived from said ultrasonic wave receiving means to thereby produce data;
    first storage means for storing data which is obtained by transmitting ultrasonic waves to a first object and receiving ultrasonic echoes reflected from the first object;
    second storage means for storing data which is obtained by transmitting ultrasonic waves to a second object and receiving ultrasonic echoes reflected from the second object;
    correlative coefficient calculating means for calculating a correlative coefficient between the data stored in said first storage means and the data stored in said second storage means;
    image processing means for producing an image signal based upon the correlative coefficient calculated by said correlative coefficient calculating means; and
    an image display unit for displaying an ultrasonic diagnostic image based upon the image signal produced by said image processing means.

2. An ultrasonic diagnosing apparatus according to claim 1, wherein said ultrasonic wave transmitting means transmits ultrasonic waves each having any one of a pulse waveform, an AC (alternating current) waveform, and an AC waveform modulated by a predetermined code.

3. An ultrasonic diagnosing apparatus according to claim 1, wherein:
    said ultrasonic wave receiving means includes a plurality of phased-array type ultrasonic wave detecting elements;
    said first storage means stores data obtained by matching phases of plural detection signals with each other which are derived from said plurality of phased-array type ultrasonic wave detection elements on the basis of the ultrasonic echoes reflected from the first object; and
    said second storage means stores data obtained by matching phases of plural detection signals with each other which are derived from said plurality of phased-array type ultrasonic wave detection elements on the basis of the ultrasonic echoes reflected from the second object.

4. An ultrasonic diagnosing apparatus according to claim 1, wherein both said ultrasonic wave transmitting means and said ultrasonic wave receiving means constitute an ultrasonic wave transmitting/receiving unit as an integral form.

5. An ultrasonic diagnosing apparatus according to claim 1, wherein said image processing means produces an image signal by executing a threshold value processing operation with respect to the correlative coefficient calculated by said correlative coefficient calculating means.

6. An ultrasonic diagnosing apparatus according to claim 1, wherein said image processing means produces an image signal by multiplying the correlative coefficient calculated by said correlative coefficient calculating means by the data stored in said second storage means.

7. An ultrasonic diagnosing apparatus according to claim 1, wherein said image processing means produces an image signal by multiplying data, which has been obtained by executing a threshold value processing operation with respect to the correlative coefficient calculated by said correlative coefficient calculating means, by the data stored in said second storage means.

8. An ultrasonic diagnosing method comprising the steps of:
    (a) storing data which is obtained by transmitting ultrasonic waves each having a predetermined waveform to a first object and receiving ultrasonic echoes reflected from the first object;
    (b) storing data which is obtained by transmitting ultrasonic waves each having a predetermined waveform to a second object and receiving ultrasonic echoes reflected from the second object;
    (c) calculating a correlative coefficient between the data stored at step (a) and the data stored at step (b);
    (d) producing an image signal based upon the correlative coefficient calculated at step (c); and
    (e) displaying an ultrasonic diagnostic image based upon the image signal produced at step (d).

9. An ultrasonic diagnosing method according to claim 8, wherein each of steps (a) and (b) includes transmitting ultrasonic waves each having any one of a pulse waveform, an AC (alternating current) waveform, and an AC waveform modulated by a predetermined code.

10. An ultrasonic diagnosing method according to claim 9, wherein:
    step (a) includes storing data obtained by receiving ultrasonic echoes reflected from the first object by using a plurality of phased-array type ultrasonic wave detecting elements and matching phases of plural detection signals with each other which are derived from said plurality of phased-array type ultrasonic wave detection elements; and
    step (b) includes storing data obtained by receiving ultrasonic echoes reflected from the second object by using said plurality of phased-array type ultrasonic wave detecting elements and matching phases of plural detection signals with each other which are derived from said plurality of phased-array type ultrasonic wave detection elements.

11. An ultrasonic diagnosing method according to claim 8, wherein said first object is an aluminum plate arranged within a fluid.

12. An ultrasonic diagnosing method according to claim 8, wherein said first object is a phantom having acoustic impedance which is substantially equal to that of a human body.

13. An ultrasonic diagnosing method according to claim 8, wherein step (d) includes producing an image signal by executing a threshold value processing operation with respect to the correlative coefficient calculated at step (c).

14. An ultrasonic diagnosing method according to claim 8, wherein step (d) includes producing an image signal by multiplying the correlative coefficient calculated at step (c) by the data stored at step (b).

15. An ultrasonic diagnosing method according to claim 8, wherein step (d) includes producing an image signal by multiplying data, which has been obtained by executing a threshold value processing operation with respect to the correlative coefficient calculated at step (c), by the data stored at step (b).

* * * * *